United States Patent [19]
Pittet et al.

[11] 3,980,089
[45] Sept. 14, 1976

[54] NOVEL HETEROCYCLIC FLAVORING COMPOSITIONS AND PROCESSES

[75] Inventors: Alan O. Pittet, Atlantic Highlands; John V. Pascale, Jackson; Denis E. Hruza, Bricktown, all of N.J.

[73] Assignee: International Flavors & Fragrances Inc., New York, N.Y.

[22] Filed: May 8, 1974

[21] Appl. No.: 468,180

Related U.S. Application Data

[63] Continuation-in-part of Ser. No. 246,484, April 21, 1972, Pat. No. 3,869,554.

[52] U.S. Cl. ............................ 131/144; 131/17 R
[51] Int. Cl.² ......................................... A24B 15/04
[58] Field of Search ............... 131/144, 17 R, 2, 17, 131/15; 260/313.1

[56] References Cited
UNITED STATES PATENTS
3,458,515  7/1969  Archibald et al. ............ 260/313.1 X

FOREIGN PATENTS OR APPLICATIONS
868,720  4/1971  Canada .............................. 131/144

OTHER PUBLICATIONS
N. Irving Sax "Dangerous Properties of Industrial Materials" published by the Reinhold Book Corp. 1968 p. 1069 cited.

*Primary Examiner*—Robert W. Michell
*Assistant Examiner*—V. Millin
*Attorney, Agent, or Firm*—Brooks Haidt Haffner & Delahunty

[57] ABSTRACT

The flavor and aroma of tobacco products are altered by adding thereto an effective amount of at least one N-substituted pyrrole having the formula:

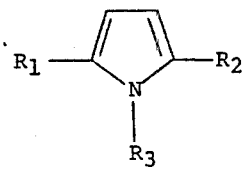

wherein $R_1$ and $R_2$ are hydrogen or alkyl and are the same or different and $R_3$ is alkyl containing eight to fourteen carbon atoms, alkenyl containing three or four carbon atoms, cycloalkyl containing from three to twelve carbon atoms, phenalkyl containing seven to eleven carbon atoms, carboalkoxyalkyl having three to seven carbon atoms, alkoxyphenylalkyl having eight to twelve carbon atoms, hydroxyalkyl having two to five carbon atoms, alkoxyalkyl having two to six carbon atoms, (alkylthio)-alkyl having two to six carbon atoms, mercaptoalkyl having from two to six carbon atoms, mercaptophenyl, pyrazinyl, pyridinyl, or thiazolyl.

15 Claims, No Drawings

NOVEL HETEROCYCLIC FLAVORING COMPOSITIONS AND PROCESSES

This application is a continuation-in-part of copending application Ser. No. 246,484, filed on Apr. 21, 1972 now U.S. Pat. No. 3,869,554.

BACKGROUND OF THE INVENTION

The present invention relates to N-substituted pyrroles and their use in processes and compositions for altering the flavors and aromas of various consumable materials such as tobaccos, foodstuffs, perfumed articles, and the like, as well as novel N-substituted pyrroles and processes for producing them.

Because of the tremendous consumption of foods, tobaccos, and other materials, there has been an increasing interest in substances and methods for imparting flavors to such consumable materials. This interest has been stimulated not only because of the inadequate quantity of natural flavoring materials available, but perhaps even more importantly, because of the need for materials which can combine several nuances, will be more stable than natural materials, will blend better with other flavors or flavoring composition components, and will generally provide superior products.

Certain pyrrole derivatives are known, some of these have been suggested for use in flavoring foodstuffs. For uniformity herein, pyrroles contain a substituent on the ring nitrogen atom will be denominated as N-substituted pyrroles, and it will be understood that such materials can also be called 1-substituted pyrroles.

A variety of pyrroles is shown in U.S. Pat. No. 3,285,931, and they are stated to be useful as intermediates in the production of pyrrolidines for aging inhibitors and other uses. See also U.S. Pat. No. 2,770,628.

Canadian Pat. No. 868,720 shows treating tobacco with (2-pyrryl) ketones and aldehydes for the purpose of affecting the smoke flavor. N-methyl- and N-furfurylpyrrole and "higher pyrroles" are said to be present in coffee aroma, and a mixture is prepared to contain the first two N-pyrroles in U.S. Pat. No. 1,696,419. U.K. patent specification No. 1,156,482 shows a variety of N-substituted pyrroles used in foodstuffs.

Gianturco et al., *Tetrahedron* 20, 2951 (1964) discuss the presence of furanic and pyrrolic compounds in coffee. Stoll et al., *Helvetica Chimica Acta*, 50 (2), 628 (1967) shows N-substituted pyrroles in coffee aroma. Various N-substituted pyrroles are also shown in Ilomets et al., Chem. *Abstr.* 1964, 10629g; Kütscher et al., *Chem. Ber.* 99 (11), 3712 (1966); Buu-Hoi et al., *Chem. Abstr.* 41, 5976e; U.K. patent specification No. 1,161,638; Buu-Hoi et al., *J. Chem. Soc.* 1961, 4836; Mannschreck et al., *Tetrahedron Letters* 1963 (29), 2003; Gross et al., *Chem. Ber.* 95, 2270; Wolthuis et al., *J. Org. Chem.* 31(6), 2009; Hazlewood et al., *Chem. Abstr.* 32, 1965; Kaluza et al., *J. Gas Chromat.* 5(11), 562; and U.S. Pat. No. 2,859,833.

U.S. Pat. No. 2,492,414 shows N-methylolpyrrole and U.S. Pat. No. 2,766,145 shows derivatives of hydroxypyrrole used in tobacco to release an acid. Neurath, *Beitrage zur Tabakforschung*, Band 5, Heft 3, shows 2-(2-pyridyl) pyrroles in tobacco flavor. U.S. Pat. No. 3,458,515 deals with certain nitrogen heterocyclic-substituted pyrroles.

THE INVENTION

It has now been found that certain N-substituted pyrroles are capable of imparting a wide variety of flavors to various consumable materials. Briefly, the invention contemplates altering the flavors of such consumable materials by adding thereto a small but effective amount of at least one N-substituted pyrrole having the formula:

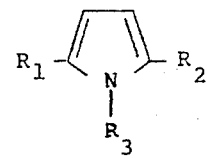

wherein $R_1$ and $R_2$ represent hydrogen or alkyl and are the same or different and $R_3$ is alkyl containing eight to 14 carbon atoms, alkenyl containing three or four carbon atoms, cycloalkyl containing from three to 12 carbon atoms, phenalkyl containing seven to 11 carbon atoms, carboalkoxyalkyl having three to seven carbon atoms, alkoxyphenylalkyl having eight to 12 carbon atoms, hydroxyalkyl having two to five carbon atoms, alkoxyalkyl having two to six carbon atoms, (alkylthio)-alkyl having two to six carbon atoms, mercaptoalkyl having two to six carbon atoms, mercaptophenyl, pyrazinyl, pyridyl, and thiazolyl. The invention also contemplates flavoring and fragrance compositions containing such pyrroles, as well as the novel pyrroles and the processes for preparing them.

The novel pyrroles according to the present invention can be represented by the formula:

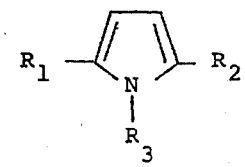

wherein $R_1$ and $R_2$ have the meaning set forth above and $R_3$ represents alkyl having ten or 14 carbon atoms, cycloalkyl containing three or eight to 12 carbon atoms, hydroxyalkyl having two to five carbon atoms, alkoxyalkyl having two to six carbon atoms, (alkylthio)alkyl having two to six carbon atoms, mercaptoalkyl having two to six carbon atoms, mercaptophenyl, pyrazinyl, pyridinyl, or thiazolyl.

For convenience herein, the various N-substituted pyrroles can be regarded as falling into three general classes: N-hydrocarbon substituted, N-chalcogen substituted, and N-heterocyclic substituted. The N-substituted hydrocarbon pyrroles would respond to the formula:

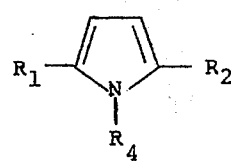

wherein $R_1$ and $R_2$ have the meaning set forth above and $R_4$ includes the alkyl, alkenyl, cycloalkyl, and phenalkyl groups described above in connection with $R_3$.

Thus, such hydrocarbon radicals would encompass a variety of materials, including certain preferred materials such as: N-tetradecylpyrrole, described hereinafter; N-decylpyrrole, a liquid having a fruity, grape-like taste with aldehydic notes and the formula:

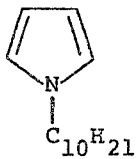

N-octylpyrrole, a compound having a fruity, peach, orange, jasmine-like fragrance; a chicken, fresh woody, vegetable flavor: a fatty, haylike flavor in tobacco; and the formula:

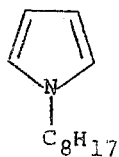

N-cyclopropylpyrrole, a novel compound having a harsh styrax fragrance with indole character like a lilac fraction; a sweet vanilla flavor at 0.2 ppm in aqueous solution with fruity and meat broth character, respectively, at 1 and 0.5 ppm; and the formula

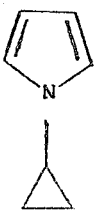

N-cyclohexylpyrrole, having a sweet, caraway aroma; a sweet, anise-like taste; an interesting fruity-green, minty taste chatacter in tobacco; and the formula:

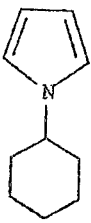

N-cyclooctylopyrrole, a novel compound having a slightly floral aroma; a green, leafy, vegetable taste in aqueous solution; a minty taste in tobacco; and the formula

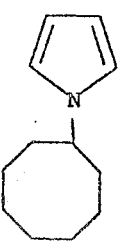

N-cyclododecylpyrrole, a novel compound having a low-key woody, fatty fragrance; a nutty, fatty flavor character; and the formula:

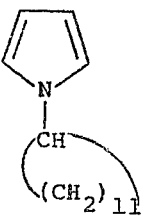

N-allylpyrrole, having a strong horseradish, mustard aroma; fruity flavor at 0.2 ppm is aqueous solution and onion, horseradish flavor notes at 1 to 30 ppm; a horseradish flavor character in tobacco; and the formula:

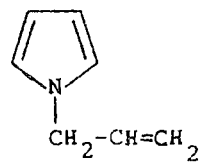

and N-benzylpyrrole, having a sweet, ethereal, floral aroma; a creamy, malted taste in aqueous solution at 0.01 ppm, and a green, fruity taste at higher levels; and the formula

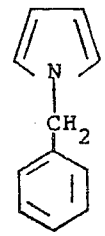

The N-pyrrole chalcogen materials would respond to the formula

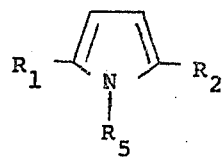

wherein $R_1$ and $R_2$ have the meaning set forth above and $R_5$ includes the carboalkoxyalkyl, alkoxyphenylalkyl, hydroxyalkyl, alkoxyalkyl, (alkylthio)alkyl, mercaptoalkyl, and mercaptophenyl groups disclosed above in connection with $R_3$.

Thus, such chalcogen-containing radicals would encompass a variety of materials, including such preferred compounds as: N-p-methoxybenzylpyrrole, having a green, horseradish, hyacinth aroma; a spring floral, sweet mushroom and berry taste in aqueous solution; and the formula:

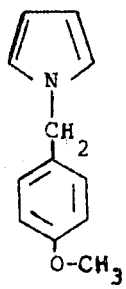

N-(β-methoxyethyl) pyrrole, a novel compound having a strong, crudely floral note similar to bromstyrol; a green, vegetable taste with horseradish and onion flavor notes becoming more dominant as the level increases; and the formula:

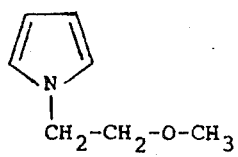

N-(γ-hydroxypropyl)pyrrole, a novel compound having a low-keyed onion, garlic aroma nuance; a cereal bread flavor with onion and meat nuances at higher levels; and the formula:

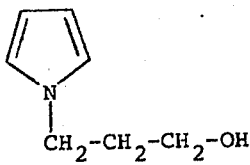

N-(β-hydroxyethyl)pyrrole, a novel compound having a green, floral aroma nuance in the hyacinth, narcisse area; a mushroom, earth flavor; and the formula:

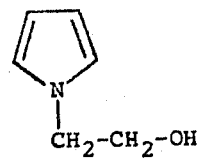

N-(methylcarbomethoxy)pyrrole having a sweet, burnt, animallike aroma; a honey, hay taste; and the formula:

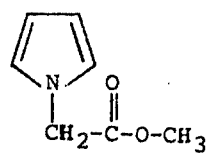

N-(ethylcarboethoxy)pyrrole, having a sweet, balsamic, fruity aroma note in the labdanax field; a sweet, fruity, almond flavor; a fruity, sweet, haylike aroma in tobacco; and the formula:

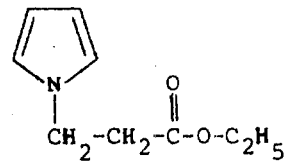

N-(β-mercaptoethyl)pyrrole, a novel compound having a sulfury aroma; coffee, roasted, meaty taste; and the formula:

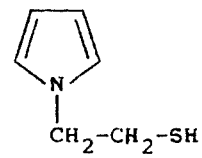

N-(p-mercaptophenyl)pyrrole, a novel compound having a green, burnt, meat-like aroma; a sweet, sulfury, rubber-like taste character suitable for certain cheese flavors; and the formula:

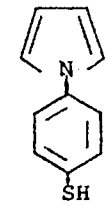

and N-[γ-(methylthio)propyl]pyrrole, a novel compound having a sweet, frutiy green aroma with a slight onion-horseradish note suiting it for galbanum-like fragrances; a green, onion, potato, vegetable taste; a raw potato drying to grassy character on tobacco; and the formula:

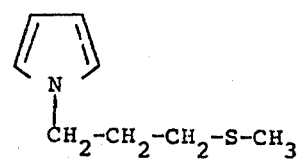

The N-heterocyclic-substituted pyrroles would correspond to the formula:

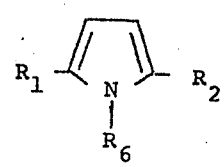

wherein $R_1$ and $R_2$ have the meaning set forth above and $R_6$ includes the pyrazinyl, pyridinyl, or thiazolyl groups disclosed above in connection with $R_3$. Thus, such N-heterocyclic-containing radicals would encompass a variety of materials, including such preferred compounds as: N-(2-pyrazinyl)pyrrole, a novel compound having peanut aroma character with mildly animal indolic notes in alcoholic solution; roasted nut taste with heliotropine notes dominating at higher levels; a pronounced nut aroma when heated on tobacco (although there is little such character before heating); and the formula:

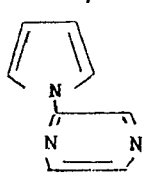

2,5-dimethyl-N-(2-pyrazinyl)pyrrole having a fruity, woody raspberry flavor with a grapefruit character at 30 ppm in aqueous solution; and the formula:

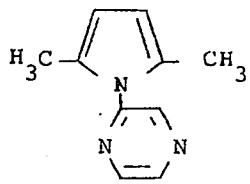

N-(2-pyridinyl)pyrrole, having a minty, menthol, naphthalene odor; a phenolic, nutty taste suitable for nut flavors like walnut and hazelnut; and the formula:

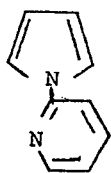

N-(4-pyridinyl)pyrrole, having a sweet roasted, balsamic nut aroma, a nut flavor suiting it for nut, honey, and baked-goods flavors; and the formula:

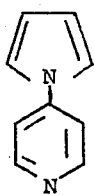

and N-(2-thiazolyl)pyrrole, having a birch tar, woody, leather, fruity, peach aroma character; a pleasant sweet taste having a cooling menthol, light bitter aftertaste in aqueous solution; a Latakia and marijuana flavor on tobacco when heated; and the formula:

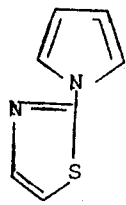

The N-pyrroles unsubstituted in the 2- and 5-positions according to the present invention are preferably prepared by treating 2,5-dialkoxytetrahydrofuran with an aliphatic, alicyclic, heterocyclic, or aromatic primary amine. The preferred alkoxy groups have from one to three carbon atoms, and methoxy is especially preferred. The primary amine is one having the amino group substituent on the carbon atoms through which it is desired to bind the $R_3$ radical to the pyrrole nitrogen atom. Thus, for example, to prepare N-(p-mercaptophenyl)pyrrole, p-aminomercaptobenzene would be used; for N-($\gamma$-hydroxypropyl)pyrrole, 3-aminopropanol-1.

The reaction is carried out in the presence of an acidic reaction medium. Such media include carboxylic acids, preferably lower carboxylic acids having two to four carbon atoms in the molecule. A preferred acid is glacial acetic acid. The reaction is carried out at temperatures of from 0° to 140°C.

The reaction is conducted at the desired reaction temperature for about 4 hours. After the reaction is completed, the excess acidity is then neutralized with an alkaline reagent such as an alkali metal hydroxide or carbonate. Sodium hydroxide is a preferred neutralizing agent.

The 2,5-dialkyl-N-substituted pyrroles according to the present invention are preferably prepared by reacting an appropriate aliphatic, alicyclic, heterocyclic, or aromatic primary amine with a dione having the formula:

where $R_1$ and $R_2$ are alkyl. The preferred alkyl groups are methyl, and the preferred dione is accordingly 2,5-hexanedione.

The amines used in the processes for providing the 2,5-dialkyl substituted pyrroles are those corresponding to the desired N-substituent. Thus, 2-aminopyrazine reacts with 2,5-hexanedione to provide 2,5-diemthyl-N-pyrazinylpyrrole; benzylamine, to provide 2,5-dimethyl-N-benzylpyrrole; and the like.

The reaction of the dione and amine is desirably carried out in the presence of an acidic catalyst, such as a mineral acid. A preferred acidic material in certain embodiments of the invention is hydrochloride acid. The dione is added slowly to the amine, and after dione addition is complete the acidic catalyst is added and the temperature is raised to a reaction temperature of 80° to 120°C and preferably about 100°C. The reaction should be carried out for a time sufficient to provide good yields. It is generally desirable to maintain the reaction mass at the reaction temperature for from 30 minutes to 2 hours, and in certain preferred embodiments of the invention times of one hour give good completeness. After the reaction is complete, the acidic material added in catalytic amounts is neutralized during extraction and washing.

It has generally been found desirable to utilize approximately equimolar portions of the dione and amine. Such quantities provide good yields and economy of reactants.

The N-substituted pyrroles according to the present invention can also be prepared by treating a pyrrole of the formula:

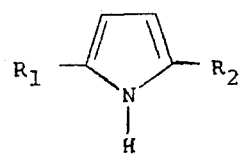

wherein $R_1$ and $R_2$ are as set forth herein, with an alkali metal, desirably sodium or potassium, to form the N- alkali metal pyrrole. Potassium is the preferred alkali metal because it is more reactive than sodium. The metalation is desirably carried out in the presence of an inert reaction vehicle. Suitable vehicles include aromatic hydrocarbons such as toluene, xylene, and the like.

The alkali metal is desirably dispersed in the reaction vehicle, and the pyrrole or alkyl-substituted pyrrole is subsequently added, preferably with continuous agitation. The metalation is carried out at 60°–120°C to provide good reaction completeness, while maintaining control of the reaction. The metalation desirably is carried out for from 30 minutes to about four hours.

After the N-alkali metal pyrrole is formed, the desired N-pyrrole derivative is formed by addition of the appropriate halide, such halides being represented as $R_3X$ wherein $R_3$ is a radical as described above and X is a halo atom. The halides preferably used are bromo and chloro. The halide is preferably added in a reaction vehicle, which can be the same as or different from the vehicle used in the metalation. This step of the reaction is carried out at 20° to 100°C.

The pyrroles so obtained can be purified or isolated by conventional purification techniques. Thus, the products can be purified and/or isolated by distillation, steam distillation, extraction, crystallization, preparative chromatographic techniques, and the like.

It will be appreciated from the present disclosure that the N-substituted pyrroles and mixtures thereof according to the present invention can be used to alter, vary, fortify, modify, enhance, or otherwise improve the flavor of a wide variety of materials which are ingested, consumed, or otherwise organoleptically sensed. The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor impression to modify organoleptic character.

Such pyrroles are accordingly useful in flavoring compositions. Such flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breadfast foods, baked goods, vegetables, cereals, soft drinks, snack foods, dog and cat foods, other veterinary products, and the like.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products include those designed or used for smoking such as in cigarette, cigar, and pipe tobacco, as well as products such as snuff, chewing tobacco, and the like.

When the N-substituted pyrroles according to this invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

Such conventional flavoring materials include saturated, unsaturated, and amino acids; alcohols, including primary and secondary alcohols; esters; carbonyl compounds including ketones and aldehydes; lactones; other cyclic organic materials including benzene derivatives, alicyclics, heterocyclics such as furans, thiazoles, thiazolidines, pyridines, pyrazines and the like; sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla, and caramel; essential oils and extracts such as anise oil, clove oil and the like; artificial flavoring materials such as vanillin; and the like.

It has been found in certain preferred embodiments that various adjuvants are particularly suited for use with the several N-substituted pyrroles according to the present invention. Thus, the N-substituted hydrocarbon pyrroles are particularly useful in flavoring compositions when used in conjunction with 2-isobutyl-3-methoxypyrazine, 4-hydroxy-2,5-dimethyl-2H-furan-3-one, 2-isobutylthiazole, or mixtures of two or more thereof.

The N-chalcogen substituted pyrroles are particularly useful in flavoring compositions when used in conjunction with ethylvanillin, maltol, vanillin, anisaldehyde, or mixtures of two or more thereof. The N-heterocyclic substituted pyrroles are particularly useful in flavoring compositions when used in conjunction with dimethylresorcinol, vanillin, ethylvanillin, maltol, dimethyl sulfide, or mixtures of two or more thereof.

Stabilizers include preservatives such as sodium chloride, and the like, antioxidants such as calcium and sodium ascorbate, ascorbic acid, butylated hydroxyanisole, butylated hydroxytoluene, propyl gallate and the like, sequestrants such as citric acid, EDTA, phosphates, and the like.

Thickeners include carriers, binders, protective colloids, suspending agents, emulsifiers and the like, such as agar-agar, carrageenan, cellulose and cellulose derivatives such as carboxymethyl cellulose and methyl cellulose, and the like, and other proteinaceous materials, lipids, carbohydrates, starches and pectins.

Surface active agents include emulsifying agents such as mono- and/or diglycerides of fatty acids including capric acid, caprylic acid, palmitic acid, myristic acid, oleic acid, and the like, lecithin, defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents such as sodium acetate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anticaking agents such as aluminum calcium sulfate and tribasic calcium phosphate; enzymes; yeast foods such as calcium lactate and calcium sulfate; nutrient supplements such as iron salts including ferric phosphate, ferric pyrophosphate, ferrous gluconate and the like, riboflavin, vitamins, zinc sources such as zinc chloride, zinc sulfate, and the like.

The N-substituted pyrroles, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The pyrroles can be incorporated with the carriers by conventional means such as spray-drying, drum-drying, and the like. Such carriers can also include materials for coacervating the pyrroles (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

It will be understood by those skilled in the art that the N-substituted pyrroles according to the present invention can be added to the materials to be flavored at any convenient point in the production of the finished product. Thus, when the pyrroles are used to alter or otherwise vary the flavor of the foodstuff, they can be added in the original mixture, dough, emulsion, batter, or the like prior to any cooking or heating operation. Alternatively, they can be added at a later stage of processing if volatilization losses would be excessive during the earlier processing.

When the pyrroles are used to treat tobacco products for example, the additive can be applied in a suitable manner, as by spraying, dipping, or otherwise. They can be applied during the "casing" or final spray treatment of the tobacco, or they can be applied at some earlier stage of curing or preparation. The quantity of N-substituted pyrroles or mixtures thereof utilized should be sufficient to impart the desired flavor characteristic to the product but on the other hand, the use of an excessive amount of the pyrroles is not only wasteful and uneconomical, but in some instances too large a quantity may unbalance the flavor or other organoleptic property of the product consumed. The quantity used will vary depending upon the ultimate foodstuff, tobacco product, or other consumable product; the amount and type of flavor initially present in the product; the further process or treatment steps to which the produce will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff, tobacco, or other consumable material.

It is accordingly preferred that the ultimate compositions contain from about $10^{-3}$ parts per million (ppm) to about 1000 ppm of pyrroles. More particularly, in food compositions it is desirable to use from about 0.01 ppm for enhancing flavors and in certain preferred embodiments of the invention, from about 1 to 50 ppm of the pyrroles are included to add positive flavors to the finished product. On the other hand, tobacco compositions can contain as little as 0.01 ppm and as much at 500 ppm depending upon whether a cigarette tobacco, a pipe tobacco, a cigar tobacco, a chewing tobacco, or snuff is being prepared. All parts, proportions, percentages, and ratios herein are by weight unless otherwise indicated.

The amount of N-substituted pyrrole or pyrroles to be utilized in flavoring compositions can be varied over a wide range depending upon the particular quality to be added to the foodstuff, tobacco, or other consumable material. Thus, amounts of one or more pyrroles according to the present invention from about 0.1 ppm up to 80 or 90 percent can be incorporated in such compositions. It is generally found to be desirable to include from about 0.1 ppm to about 0.1% of the pyrroles in such compositions.

The pyrroles of this invention are also useful individually or in admixtures as fragrance. They can be used to contribute various nut, fruity, sharp, or floral fragrances. As olfactory agents, the pyrroles of this invention can be formulated into or used as components of a "perfume composition."

A perfume composition is composed of a small but effective amount of an N-substituted pyrrole of this invention and an auxiliary perfume ingredient, including, for example, alcohols, aldehydes, ketones, nitriles, esters, and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation, and (d) top-notes which are usually low-boiling fresh smelling materials.

In perfume compositions the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by high-lighting or moderating the olfactory reaction contributed by another ingredient in the composition.

The amount of the compounds of this invention which will be effective in perfume compositions depends on many factors, including the other ingredients, their amounts and the effects which are desired. It has been found that perfume compositions containing as little as one percent of the compounds of this invention, or even less, can be used to impart a scent odor to soaps, cosmetics, and the other products. The amount employed can range up to 50% or higher of the fragrance components and will depend on considerations of cost, nature of the end product, the effect desired on the finished product and the particular fragrance sought.

The pyrroles of this invention can be used alone or in a perfume composition as an olfactory component in detergents and soaps; space odorants and deodorants; perfumes; colognes; toilet waters; bath preparations such as bath oil and bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 100 ppm of one or more of the preferred pyrroles will suffice to impart a floral, geranium odor character. Generally, no more than 0.5% is required in the perfume composition.

In addition, the perfume composition or fragrance composition can contain a vehicle or carrier for the pyrroles alone or with other ingredients. The vehicle can be a liquid such as alcohol, glycol, or the like. The carrier can be an absorbent solid such as gum or components for encapsulating the composition.

It will thus be apparent that the pyrroles according to the present invention can be utilized to alter the sensory properties, particularly organoleptic properties such as flavor and/or fragrance of a wide variety of consumable materials.

The following examples are given to illustrate embodiments of the invention as it is presently preferred to practice it. It will be understood that these examples are illustrative, and the invention is not to be considered as restricted thereto except as indicated in the appended claims.

EXAMPLE I

Preparation of N-Decylpyrrole

To a mixture of 78.5 g (0.5 mole) N-decylamine and 66 g (0.5 mole) 2,5-dimethoxytetrahydrofuran in a 3-neck, 1-liter flask equipped with a stirrer, thermometer, dropping funnel and condenser, is added 225 ml glacial acetic acid dropwise with stirring while maintaining the reaction mixture temperature below 20°C. The reaction mixture is thereupon heated under reflux for 30 minutes and then cooled, made basic (pH 9-10) with 375 ml of 30% aqueous sodium hydroxide, and finally steam-distilled to yield approximately 2 liters of distillate.

The distillate is extracted four times with 400 ml portions of diethylether, and the combined ether extracts are dried over anhydrous sodium sulfate. The filtered solution is evaporated and the residue distilled under reduced pressure.

N-Decylpyrrole is obtained as 21 g of a colorless liquid with b.p. 102°-104°C at 0.5 mm Hg. Mass spectroscopy (MS) shows the m/e peaks: 81, 80, 41, 207, 43.

EXAMPLE II

Preparation of N-Octylpyrrole

Into a 1-liter 3-neck flask equipped with stirrer, condenser, addition funnel and heating mantle are introduced 65 g (0.5 mole) of 1-octylamine, 66 g (0.5 mole) of 2,5-dimethoxytetrahydrofuran, and 210 ml of glacial acetic acid. The reaction mass is refluxed at atmospheric pressure for 1 hour, cooled, and made alkaline to pH 9 with 180 ml of 50% aqueous sodium hydroxide solution.

Then 250 ml of water is added to the reaction mass, and the mass is steam-distilled. The liter of distillate collected is then saturated with sodium chloride and extracted with four 400 ml portions of diethyl ether. The ether extract is dried over anhydrous sodium sulfate, filtered, and evaporated down.

The residue is distilled at 5 mm Hg pressure at 98°-100°C to obtain 4.4 g of N-octylpyrrole. Mass spectral analysis of the liquid shows the peaks: parent, 179; other 81, 80, 41, 27, and 29.

EXAMPLE III

Preparation of N-Cyclopropylpyrrole

Into a 1-liter, 3-neck flask equipped with stirrer, condenser, heating mantle, addition funnel and thermometer are introduced 25 g (0.4 mole) of cyclopropylamine, 58 g (0.44 mole) of 2,5-dimethoxytetrahydrofuran, and 200 ml of glacial acetic acid. The reaction mass is refluxed for one-half hour, cooled, and made alkaline to pH 9 with 108 ml of 50% aqueous sodium hydroxide solution.

The reaction mass is then steam-distilled, and one liter of distillate is collected. The steam distillate is then saturated with sodium chloride and extracted with four 400 ml portions of diethyl ether. The ether extract is dried over anhydrous sodium sulfate, filtered, and evaporated down.

The residue is distilled at 20 mm Hg pressure at a temperature of 54°-55°C to obtain 18.4 g of liquid N-cyclopropylpyrrole. Mass spectral analysis shows: parent peak: 107; other peaks: 106, 39, 79, 80, 41.

EXAMPLE IV

Preparation of N-Cyclooctypyrrole

Into a 1-liter 3-neck flask equipped with stirrer, condenser, thermometer and addition funnel are introduced 63.6 g (0.5 mole) of cyclooctylamine, 66.0 g (0.5 mole) of 2,5-dimethoxytetrahydrofuran, and 210 ml of glacial acetic acid. The reaction mixture is refluxed for one-half hour at atmospheric pressure and then cooled.

The reaction mass is made alkaline to pH 9-10 with 400 ml of 5N sodium hydroxide. The resulting mixture is steam-distilled and one liter of distillate is collected. The distillate is then extracted with four 400 ml portions of diethyl ether, and the extract is dried over anhydrous sodium sulfate, filtered, and evaporated. The residue is distilled at 0.2 mm Hg pressure at 78°-80°C to obtain 17.4 g of N-cyclooctylpyrrole. Mass spectral analysis of the liquid shows a parent peak at 177 and other peaks at 67, 68, 41, 81, and 94.

EXAMPLE V

Preparation of N-(p-Methoxybenzyl)pyrrole

Into a 1-liter 3-neck flask equipped with stirrer, condenser, and heating mantle are introduced 68.5 g (0.5 mole) of p-methoxybenzylamine, 66.0 g (0.5 mole) of 2,5-dimethoxytetrahydrofuran, and 210 ml of glacial acetic acid. The reaction mixture is refluxed for one-half hour at atmospheric pressure.

The mass is then cooled and made alkaline with aqueous 5N sodium hydroxide. The resulting reaction product is steam-distilled and collected in the amount of 1 liter. The distillate is saturated with sodium chloride and extracted with four 400 ml portions of diethyl ether. The diethyl ether extract is then dried over anhydrous sodium sulfate, filtered, and evaporated.

The residue is distilled at 8 mm Hg pressure at 123°–125°C to obtain 2.6 g of N-(p-methoxybenzyl)pyrrole. Mass spectral analysis of the liquid shows a parent peak at 187 and other peaks at 121, 78, 77, 39, and 122.

EXAMPLE VI

Preparation of N-(4-Mercaptophenyl)pyrrole

A 1-liter 3-neck flask equipped with stirrer, condenser, heating mantle, addition funnel and thermometer is charged with 25 g (0.2 mole) of 4-aminothiophenol, 26.4 g (0.2 mole) of 2,5-dimethoxytetrahydrofuran, and 150 ml of glacial acetic acid. The reaction mass is refluxed for 30 minutes, cooled and made alkaline to a pH of 9 with 130 ml of 50% aqueous sodium hydroxide while maintaining the temperature of the reaction mixture below 25°C with a cooling bath.

The reaction mass is steam-distilled and 1 liter of distillate is collected. The distillate is saturated with sodium chloride and extracted with two 1-liter portions of diethyl ether. The ether extract is dried over anhydrous sodium sulfate and filtered and evaporated down. Pale yellow crystals of N-(4-mercaptophenyl)pyrrole precipitate having the following mass spectrum: parent peak 175; other peaks: 39, 45, 174, 115, and 147.

EXAMPLE VII

Preparation of N-(γ-Hydroxypropyl)pyrrole

A 1-liter 3-neck flask equipped with stirrer, condenser, heating mantle, addition funnel and thermometer is charged with 37.5 g (0.5 mole) of 3-amino-1-propanol and 66 g (0.5 mole) of 2,5-dimethoxytetrahydrofuran, and 200 ml of glacial acetic acid is then added dropwise to the reaction mass with stirring. Upon completion of the addition of the glacial acetic acid, the reaction mass is refluxed for 30 minutes and then cooled.

The reaction mass is then neutralized to a pH of 8 with 375 ml of 30% aqueous sodium hydroxide. The neutralized reaction mixture is steam-distilled, and the 500 ml of distillate collected is extracted with two 1-liter portions of diethyl ether. The ether extract is dried over anhydrous sodium sulfate, filtered and evaporated down.

The residue is then distilled at 1.4 mm Hg pressure at 92°C to obtain 3.0 g of N-(γ-hydroxypropyl)pyrrole. Mass spectroscopy of this liquid shows a parent peak at 125 and other peaks at 81, 80, 53, 41, and 39.

EXAMPLE VIII

Preparation of N-(β-Mercaptoethyl)pyrrole

A 1-liter 3-neck flask equipped with stirrer, condenser, heating mantle, addition funnel and thermometer is charged with 38.5 g (0.5 mole) of 2-aminoethanethiol-1 and 66 g (0.5 mole) of 2,5-dimethoxytetrahydrofuran, and 225 ml of glacial acetic acid is added dropwise with stirring over 15 minutes while maintaining the temperature of the reaction mass below 20°C. The reaction mass is then refluxed for one-half hour, cooled, and made alkaline to a pH of 9 with 400 ml of 30% aqueous sodium hydroxide. The reaction mass is steam-distilled and the distillate is extracted with four 250 ml portions of diethylether. The extract is dried over anhydrous sodium sulfate, filtered and evaporated down. The 3.9 g of liquid N-(β-mercaptoethyl)-pyrrole so obtained is not distilled. Mass spectroscopy shows a parent peak at 127 and other peaks at 80, 67, 39, 53, and 68.

EXAMPLE IX

Preparation of N(β-Hydroxyethyl)pyrrole

A mixture of 163 g (3 mole) ethanolamine and 396 g (3 mole) 2,5-dimethoxytetrahydrofuran is placed in a 5-liter 3-neck flask equipped with stirrer, addition funnel, thermometer and condenser, and 1 liter of glacial acetic acid is added dropwise with stirring while maintaining the temperature below 20°C. The reaction mixture is refluxed for 1 hour and after cooling, it is made basic with 850 ml 50% sodium hydroxide and steam-distilled.

The distillate (3 liters) is saturated with sodium chloride and extracted thrice with liter portions of diethylether. The combined ether extracts are dried over anhydrous sodium sulfate; after filtration the ether is removed by evaporation; and the residue so obtained is vacuum-distilled.

The product is distilled at 62°–70°C at 0.5 mm Hg and 8 g of N-(β-hydroxyethyl)pyrrole is obtained as a colorless liquid. The product exhibits the following mass spectrum in order of decreasing ion abundance (m/c): 80, 111, 53, 68, 27.

EXAMPLE X

Preparation of N-(γ-Methylthiopropyl)pyrrole

A mixture of 25 g (0.36 mole) 3-(methylthio)propylamine and 43 g (0.36 mole) 2,5-dimethoxytetrahydrofuran is placed in a 1-liter 3-neck flask equipped with a stirrer, addition funnel, thermometer and condenser, and 200 ml glacial acetic acid is added dropwise with stirring while maintaining the temperature below 20°C. The reaction mixture is refluxed for 30 minutes and, after cooling, it is made basic (pH 9–10) by the addition of 375 ml 30% aqueous sodium hydroxide and steam-distilled for 3 hours.

The distillate is extracted four times with 250 ml portions of diethylether, and the combined ether extracts are dried over anhydrous sodium sulfate. After filtration the ether is removed by evaporation and the residue so obtained is vacuum-distilled. The methylthiopropylpyrrole is obtained as 12.8 g of colorless liquid boiling at 109°–111°C at 10 mm.

The product exhibits the following mass spectrum, in order of decreasing ion abundance: (m/e) 81, 155, 80, 39, 52, 41.

EXAMPLE XI

Preparation of N-(Ethylcarboethoxy)pyrrole

Eight grams of potassium metal is dispersed in 100 ml of boiling xylene and rapidly cooled to yield a fine dispersion. After the addition of two drops of absolute ethanol, pyrrole (18.4 g, 0.3 mole) is added in small portions. When the addition is complete the reaction mixture is heated at 80°C for 1 hour. The solvent and pyrrole are removed by evaporation at 60°C and 20 mm Hg pressure to yield 21 g of potassium pyrrole.

After adding 30 ml of benzene to the potassium pyrrole, a solution of 30.0 g (0.22 mole) of ethylchloropropionate in 30 ml benzene is slowly added to the paste over a period of 1 hour with constant stirring. The reaction mixture is heated to 80°C for 30 minutes.

Then 100 ml of water is added and the mixture is extracted with diethyl ether. The ether extract is dried over anhydrous magnesium sulfate and the dried extract is evaporated to yield residue which is distilled under vacuum. The pyrrole derivative having the formula given above is obtained as 3 g of a colorless liquid with a boiling point of 108°C at 14 mm Hg pressure. MS shows the m/e peaks: 80, 94, 167, 27, 95.

EXAMPLE XII

Preparation of N-(Methylcarbomethoxy)pyrrole

Eight grams of potassium is dispersed in 100 ml of boiling xylene and rapidly cooled to yield a fine dispersion. After the addition of two drops of absolute ethanol, pyrrole (18.4 g, 0.3 mole) is added in small portions. When the addition is complete the reaction mixture is heated at 80°C for 1 hour. The solvent and excess pyrrole are removed by evaporation at 60°C and 20 mm Hg pressure to yield 21 g potassium pyrrole.

After adding 30 ml of benzene to the potassium pyrrole, a solution of 30.0 g (0.22 mole) of methylchloracetate in 30 ml benzene is slowly added to this paste over one hour with constant stirring. The reaction mixture is then heated at 80°C for 30 minutes, 100 ml of water is added, and the mixture is extracted with ether. The ether extract is dried with anhydrous magnesium sulfate and the solvent evaporated to yield a residue which is distilled under vacuum.

The pyrrole derivative as above is obtained as 21.8 g of a colorless liquid boiling at 80°C at 10 mm Hg. MS shows the m/e peaks: 80, 139, 53, 27, 51.

EXAMPLE XIII

Preparation of N-($\beta$-Methoxyethyl)pyrrole

A mixture of 38 g (0.5 mole) 2-methoxyethylamine and 66 g (0.5 mole) 2,5-dimethoxytetrahydrofuran is charged to a 1-liter 3-neck flask equipped with a stirrer, addition funnel, thermometer and condenser, and 200 ml glacial acetic acid is added dropwise with stirring while maintaining the temperature below 20°C. The reaction mixture is refluxed for 30 minutes and, after cooling, it is made basic (pH 9–10) by the addition of 335 ml 30% aqueous sodium hydroxide and steam-distilled to yield 1500 ml of distillate.

The distillate is then extracted thrice with 500 ml portions of diethyl ether and the combined ether extracts dried over anhydrous sodium sulfate. After filtration, the ether is removed by evaporation and the residue so obtained is vacuum-distilled. The pyrrole derivative product is obtained as 21.8 g of a colorless liquid boiling point at 49°–50°C under 0.8 mm Hg. MS shows the m/e peaks: 80,125,53,45,27.

EXAMPLE XIV

Preparation of N-(2-Pyridinyl)pyrrole

A 1-liter 3-neck flask equipped with stirrer, condenser, heating mantle, addition funnel and thermometer is charged with 47 g (0.5 mole) of 2-aminopyridine and 65 g (0.5 mole) 2,5-dimethoxytetrahydrofuran. These materials are mixed together and 200 ml of glacial acetic acid added dropwise with stirring over 10 minutes while maintaining the temperature at less than 20°C.

The reaction mixture is then refluxed for one-half hour, cooled, and made alkaline to a pH of 9–10 with 30% aqueous sodium hydroxide. The reaction mass is then steam-distilled, and 2 liters of distillate is collected. The distillate is extracted with four 450 ml portions of diethyl ether, and the extract is dried over anhydrous sodium sulfate, filtered, and evaporated down.

The residue is distilled at 0.5 mm Hg pressure at 87°C to obtain 27.3 g of the pyrrole derivative. Mass spectroscopy shows a parent peak at 144 and other peaks at 117, 78, 51, 39, and 118.

EXAMPLE XV

Preparation of N-(4-Pyridinyl)pyrrole

A 1-liter 3-neck flask equipped with stirrer, condenser, heating mantle, addition funnel and thermometer is charged with 47 g (0.5 mole) of 4-aminopyridine and 66 g (0.5 mole) of 2,5-dimethoxytetrahydrofuran. These materials are mixed together and 210 ml of glacial acetic acid is added dropwise with stirring over ten minutes while maintaining the temperature at less than 20°C.

The reaction mass is steam-distilled and 2 liters of distillate is collected. The distillate is extracted with four 450 ml portions of diethyl ether and the extract is dried over anhydrous sodium sulfate, filtered and evaporated down.

The residue is distilled at 0.5 mm Hg pressure at 87°C to obtain 46.35 g of the pyridinylpyrrole as crystals melting at 76.6°–77.6°C. Mass spectroscopy shows a parent peak at 144 and other peaks at 51, 117, 143, 90, and 39.

EXAMPLE XVI

Preparation of N-(2-Pyrazinyl)pyrrole

A mixture of 43 g (0.5 mole) 2-aminopyrazine and 66 g (0.5 mole) 2,5-dimethoxytetrahydrofuran is placed in a 1-liter 3-neck flask equipped with a stirrer, addition funnel, thermometer and condenser, and 200 ml glacial acetic acid is added dropwise with stirring while maintaining the temperature below 20°C. The reaction mixture is refluxed at 105°C for 30 minutes and, after cooling, it is made basic by the addition of 325 ml of 30% aqueous sodium hydroxide and steam-distilled.

A white crystalline solid separates from the distillate and is collected by filtration to yield 51.3 g of the pyrazinylpyrrole. The product has a melting range of 90.5°–93.5°C. MS shows the m/e peaks: 145, 52, 92, 39, 118.

EXAMPLE XVII

Synthesis of N-(2-Pyrazinyl)-2,5-dimethylpyrrole

To 47.5 g (0.5 mole) aminopyrazine contained in a 250 ml 3-neck flask equipped with a stirrer, addition funnel, thermometer and condenser, is added 62.7 g (0.55 mole) 2,5-hexanedione dropwise with stirring over 30 minutes. Then 5 ml of 5N hydrochloric acid is added as catalyst and the reaction mixture is heated at 100°C for 1 hour, causing the color of the reaction mixture to change from tan to wine red.

After cooling, the reaction mixture is transferred to a 2-liter separatory funnel containing one liter of water and the resulting acidic mixture is extracted four times with 400 ml portions of diethyl ether. The aqueous phase is then made basic with 6 ml of 5N sodium hydroxide and extracted four times with 200 ml portions of diethylether. The acidic and basic ether extracts are separately dried over anhydrous sodium sulfate and the solvent evaporated to yield mixtures of the pyrazinyl dimethylpyrrole and starting materials as shown by gas chromatrography.

The material obtained from the basic extraction is distilled under reduced pressure and the N-pyrazinyl-pyrrole compound is obtained as 3 g of a colorless liquid boiling at 120°–123°C and 10 mm Hg which immediately crystallizes. The crystals melt at 110°–114°C. The identity of the product as N-(2-pyrazinyl)-2,5-dimethylpyrrole is confirmed by mass spectrometric data as follows:

| m/e | Abundance (%) |
|---|---|
| 173 | 100 |
| 172 | 85 |
| 95 | 56 |
| 158 | 41 |
| 94 | 38 |
| 68 | 37 |
| 43 | 29 |
| 41 | 29 |
| 52 | 25 |

EXAMPLE XVIII

Preparation of N-(2-Thiazolyl)pyrrole

A mixture of 55.5 g (0.5 mole) 2-aminothiazole (90% pure) and 66 g (0.5 mole) 2,5-dimethyltetrahydrofuran is placed in a 1-liter 3-neck flask equipped with a stirrer, addition funnel, thermometer, and condenser, and 200 ml glacial acetic acid is added dropwise with stirring while maintaining the temperature below 20°C. After stirring for an additional 15 minutes, the reaction mixture is refluxed for 30 minutes and then cooled, made basic (pH 9–10) with 375 ml 30% sodium hydroxide, and steam-distilled to yield 1500 ml distillate.

The distillate is then extracted four times with 500 ml portions of diethyl ether and the combined ether extracts are dried over anhydrous sodium sulfate. After filtration, the ether is removed by evaporation and the residue so obtained is vacuum-distilled to yield 41.0 g of the pyrrole as a colorless liquid with a boiling point of 80°–81°C at 3 mm Hg. MS shows the m/e peaks: 150, 58, 39, 123, 45.

EXAMPLE XIX

Imitation Raspberry Flavor

The following mixture is prepared:

| Ingredient | Parts |
|---|---|
| Vanillin | 20 |
| Ethyl vanillin | 8 |
| α-Ionone (10% in Propylene Glycol) | 1 |
| Maltol | 30 |
| para-Hydroxyphenylbutanone | 100 |
| Dimethyl sulfide (1% in Ethanol) | 1 |
| Ethyl alcohol 95% | 140 |
| Propylene glycol | 700 |

2,5-Dimethyl-N-(2-pyrazinyl)pyrrole (prepared according to Example XVII) added at the rate of 0.1% contributes to the woody note of wild raspberries and adds to the kernel character of this formulation. It substantially improves the above raspberry flavor when applied in hard candies at the rate of 0.05%.

EXAMPLE XX

The following mixture is prepared:

| Ingredient | Parts |
|---|---|
| Fenugreek extract | 20.00 |
| Valerian oil | 7.00 |
| Dimethylresorcinol | .25 |
| Propylene glycol | 39.75 |
| N-(2-Pyrazinyl)pyrrole (prepared according to Example XVI) | 3.00 |
| Water | 10.00 |

The above mixture, when added to tobacco at rates of 0.10 to 0.70%, imparts a nutty pyrazine-like odor to the tobacco and confers a walnut character on the product.

EXAMPLE XXI

The following mixture is prepared:

| Ingredient | Parts |
|---|---|
| Oil birch tar, crude | 30.00 |
| Thymol | 10.00 |
| Lauric acid, tech. | 10.00 |
| Phenylacetic acid | 8.00 |
| Cade Oil | 10.00 |
| N-(2-Thiazolyl)pyrrole | 1.00 |
| Propylene glycol | 31.00 |

The above formulation when added to tobacco at rates of 0.05 to 0.30% imparts a leather-like note thereby lending to the tobacco a "Latakia" and "marijuana" flavor. Thus, such formulation is useful for preparing tobacco products which can be used to demonstrate characteristic aromas or flavors of other materials without using such materials.

EXAMPLE XXII

The following mixture is prepared:

| Ingredient | Parts |
|---|---|
| Lovage oil | 12.00 |
| St. Johns bread extract | 3.00 |
| Fenugreek extract | 12.00 |
| Coffee extract* | 4.00 |
| Cocoa extract** | 20.00 |
| Oleoresin celery extract | 4.00 |
| N-(4-Pyridinyl)pyrrole | 5.00 |
| Propylene Glycol | 40.00 |

*Aqueous coffee extract produced by mixing eight pounds ground Brazilian coffee, 2.5 liters propylene glycol and eight liters of water; refluxing under atmospheric pressure for 8 hours; and filtering the resultant aqueous extract.
**Aqueous cocoa extract produced by mixing eight pounds cocoa nibs, 2.5 liters 95% ethyl alcohol, and eight liters water; refluxing eight hours; and filtering, thereby recovering an aqueous cocoa.

The above formulation when added to tobacco at the 0.1 to 0.5% imparts a mint flavor to the tobacco.

EXAMPLE XXIII

The following mixture is prepared:

| Ingredients | Parts |
|---|---|
| Solid extracts, alfalfa | 16.00 |
| Amylvinylcarbinol | 0.50 |
| Hydrotropaldehyde-dimethyl acetal | 1.20 |
| Amylphenyl acetate | 0.50 |
| Heliotropine | 4.00 |

-continued

| Ingredients | Parts |
| --- | --- |
| Phenyl acetaldehyde | 1.00 |
| Fenugreek extract | 6.00 |
| gamma-Hexalactone | 1.00 |
| N-[γ-Methylthio)propyl]pyrrole (Produced according to Example X) | 3.00 |
| Propylene glycol | 66.80 |

This mixture is added to tobacco at rates of from 0.10% to 0.6% and lends to the tobacco a desired raw potato, grassy aroma. The entire tobacco formulation is described as a hay-flavored tobacco.

EXAMPLE XXIV

The following mixture is prepared:

| Ingredients | Parts |
| --- | --- |
| Ethyl vanillin | 30 |
| Vanillin | 120 |
| Maltol | 20 |
| Anisaldehyde (10% solution in propylene glycol) | 10 |
| Ethyl alcohol (95%) | 120 |
| Propylene glycl | 700 |

N-(Ethylcarboethoxy)pyrrole (produced according to Example XI) added to the above mixture at the rate of 1% imparts a natural vanilla bean character. The resultant flavor with the pyrrole added thereto is then used at the rate of 0.05% in baked goods.

EXAMPLE XXV

When added at the rate of 0.1% to a commercial carob seed (St. John's bread) extract a more natural stronger character is imparted to the carob extract by the pyrrole of Example XXIV.

EXAMPLE XXVI

The following mixture is preapred:

| Ingredients | Parts |
| --- | --- |
| N-[gamma-(Methylthio)propyl]pyrrole | 1 |
| 2-Methyl-5-methoxythiazole (10% in diethyl phthalate) | 1 |
| N-Decylpyrrole (10% in diethyl phthalate) | 2 |
| Benzyl butyrate | 4 |
| Bois de Rose | 10 |
| Citronellyl formate | 30 |
| Citronellyl acetate | 20 |
| Geraniol coeur | 200 |
| Citronellol coeur | 300 |
| Menthone | 5 |
| Menthol natural | 5 |
| Rose oxide | 10 |
| Geranyl acetate | 30 |
| Dimethyl benzyl carbonyl acetate | 2 |

The use of N-[gamma-methylthio)propyl]pyrrole imparts a long life, greeniness and bloom to the geranium top note.

The use of N-decylpyrrole imparts a warmth and sweetness in the rosy family, thereby rounding out this geranium formulation.

EXAMPLE XXVII

A 2-year old horseradish preparation is treated by adding 30 ppm of N-allylpyrrole. The horseradish preparation which does not have the allylpyrrole added to it is substantially tasteless, having the aroma of weak vinegar, whereas the aged horseradish which has the allylpyrrole added to it has the characteristic biting and burning sensation of fresh horseradish. The addition of N-allylpyrrole at the rate of from 10 to 100 ppm adds more of the desired taste to the aged horseradish preparation and contributes to a longer shelf life.

EXAMPLE XXVIII

The following mixture is prepared:

| Ingredient | Parts |
| --- | --- |
| Oil of Birch tar - crude | 60 |
| Ky leaf extract (1–2% nicotine) | 200 |
| Isovaleric acid | 20 |
| Caproic acid | 30 |
| Phenyl acetic acid | 60 |
| Lauraldehyde | 10 |
| N-Allylpyrrole | 10 |
| Propylene glycol | 610 |

This mixture is added to tobacco at rates of from 0.01% to 0.50% and lends to the tobacco a desirable horseradish character.

EXAMPLE XXIX

A 125 ml 3-neck flask fitted with a stirrer, is charged with 33 g (0.25 mole) of 2,5-dimethoxytetrahydrofuran, 38.5 (0.18 mole) of N-tetradecylamine, and 60 ml (1 mole) of glacial acetic acid, and the mixture is stirred for 12 hours. The mixture is then made alkaline with 5N aqueous sodium hydroxide, and 50 ml of water is added.

The resulting mixture is extracted four times with 400 ml of diethyl ether, and the ether extract is dried over sodium sulfate, filtered, and evaporated down. A white crystalline residue forms.

The residue is distilled at reduced pressure to obtain N-tetradecylpyrrole, boiling at a temperature of 165°–166°C at 5 mm Hg and having the formula:

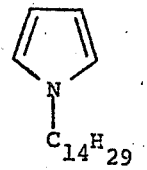

It will accordingly be understood that $R_4$ can also represent a 14 carbon atom alkyl group. MS shows the m/e peaks: 81, 263, 80, 55, 43.

This novel material has a low-keyed meat-like aroma note; a weak, slightly sweet taste in aqueous solution; and a tobacco flavor enhancing effect.

EXAMPLE XXX

A tobacco flavoring formulation is prepared by admixing the following ingredients.

| Ingredient | Amount (Parts) |
| --- | --- |
| Burley extract | 15 |
| Black tobacco extract | 10 |
| Caproic acid | 2 |
| Isovaleric acid | 2.5 |
| Ammonium hydroxide solution (28%) | 2 |
| N-Tetradecylpyrrole produced in Example 29 | 5 |
| Prune juice concentrate | 10 |

-continued

| Ingredient | Amount (Parts) |
| --- | --- |
| Propylene glycol | 25 |
| Water | 28.5 |

This material is added to smoking tobacco at the rate of 0.3–0.4% of the weight of tobacco.

It is found to enhance the character of natural tobacco extracts and to improve the flavor.

EXAMPLE XXXI

Preparation of N-Cyclododecylpyrrole

A 1-liter 3-neck flask equipped with stirrer, condenser and addition funnel, is charged with 91.7 g (0.5 mole) of N-cyclododecylamine, 66 g (0.5 mole) of 2,5-dimethoxytetrahydrofuran, and 210 ml of glacial acetic acid. The reaction mass is refluxed for 30 minutes and then cooled and made alkaline with 180 ml of a 50% aqueous sodium hydroxide solution. During the time the sodium hydroxide solution is being added, the temperature is kept below 20°C.

The reaction product is then steam-distilled and one liter of distillate is collected. The steam-distillate is saturated with sodium chloride and extracted with four 400 ml portions of diethyl ether, and the combined ether extracts are dried over anhydrous sodium sulfate. The resulting mixture is filtered and evaporated down, and the residue is distilled under reduced pressure.

N-cyclododecylpyrrole in the amount of 3.8 g is obtained as a liquid boiling at 180°–183°C and 10 mmHg. NMR, mass spectral and infrared data confirm the structure of the reaction product as N-cyclododecylpyrrole. Mass spectral data (m/e) show a parent peak at 233 and other peaks at 81, 67, 68, 94, 41.

EXAMPLE XXXII

Tobacco Use of N-Cyclooctyl Pyrrole and N-Cyclopropyl Pyrrole

The following tobacco flavor formulation (A) is prepared:

| Ingredients | Parts |
| --- | --- |
| Ethyl Butyrate | 0.05 |
| Ethyl Valerate | 0.05 |
| Maltol | 2.00 |
| Cocoa Extract | 26.00 |
| Coffee Extract | 10.00 |
| Ethanol (95% aqueous) | 20.00 |
| Water | 41.90 |

A tobacco formulation (B) is prepared as follows:

| Ingredients | Parts |
| --- | --- |
| Bright Tobacco | 40.1 |
| Burley Tobacco | 24.9 |
| Maryland Tobacco | 1.1 |
| Turkish Tobacco | 11.6 |
| Stem (Flue-cured) Tobacco | 14.2 |
| Glycerine | 2.8 |
| Water | 5.3 |

The flavor formulation (A) is added to a portion of the smoking tobacco formulation (B) at the rate of 0.1% by weight of the tobacco. The flavored and non-flavored tobacco formulations are then formulated into cigarettes by the usual manufacturing procedures:

i. At the rate of 20 ppm to one-fourth of the cigarettes in each group is added N-cyclooctyl pyrrole. The use of the N-cyclooctyl pyrrole in the cigarettes causes the cigarettes prior to smoking to have a cocoa-chocolate like jar or pack aroma. In smoke flavor, these notes are not found, however, on smoking, the cigarettes containing the N-cyclooctyl pyrrole are found to be more aromatic, sweeter and to have more body whether or not the other flavor ingredients of formulation (A) are present.

ii. At the rate of 40 ppm to one-fourth (¼) of the cigarettes in each group is added N-cyclooctyl pyrrole. The use of the N-cyclooctyl pyrrole at this level also causes the tobacco prior to smoking to have a cocoa-chocolate like jar or pack aroma. On smoking, the cocoa-chocolate like jar or pack aroma is not perceived in the smoke flavor. However, the cigarettes are found to be more aromatic, sweeter and to have more body on smoking than the same formulation without the N-cyclooctyl pyrrole whether or not the other flavor ingredients of formulation (A) are present therein.

iii. At the rate of 20 ppm to one-fourth (¼) of the cigarettes in each group is added N-cyclopropyl pyrrole. The use of the N-cyclopropyl pyrrole in the cigarettes causes the cigarettes prior to smoking to have a cocoa-chocolate like jar or pack aroma. In smoke flavor, these notes are not found, however, on smoking, the cigarettes containing the N-cyclopropyl pyrrole are found to be more aromatic, sweeter and to have more body whether or not the other flavor ingredients of formulation (A) are present.

iv. At the rate of 40 ppm to one-fourth (¼) of the cigarettes in each group is added N-cyclopropyl pyrrole. The use of the N-cyclopropyl pyrrole at this level also causes the tobacco prior to smoking to have a cocoa-chocolate like jar or pack aroma. On smoking, the cocoa-chocolate like jar or pack aroma is not perceived in the smoke flavor. However, the cigarettes are found to be more aromatic, sweeter and to have more body on smoking than the same formulation without the N-cyclopropyl pyrrole whether or not the other flavor ingredients of formulation (A) are present therein.

In general, on smoking, the cigarettes containing either the N-cyclooctyl pyrrole or N-cyclopropyl pyrrole are sweeter, less harsh, have more body and are more aromatic in nature than those cigarettes not containing the N-cyclooctyl pyrrole or N-cyclopropyl pyrrole whether or not ingredients of formulation (A) are included in the tobacco.

It will be understood by those skilled in the art from the foregoing description that the N-substituted pyrroles can be used in the preparation of a wide variety of flavor and fragrance compositions. The pyrroles prepared according to the several Examples can be used in a similar manner to those shown in the various flavoring, perfume and tobacco Examples.

What is claimed is:

1. A process for altering the flavor and aroma of a tobacco product which comprises adding thereto from about 0.01 to 500 parts per million of at least one N-substituted pyrrole having the formula

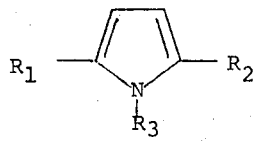

wherein $R_1$ and $R_2$ are the same or different and represent hydrogen or methyl and $R_3$ represents alkyl containing eight to fourteen carbon atoms, alkenyl containing three or four carbon atoms, cycloalkyl containing three to twelve carbon atoms, or phenalkyl containing seven to eleven carbon atoms.

2. A process according to claim 1 wherein $R_3$ is tetradecyl, decyl, octyl, cyclopropyl, cyclohexyl, cyclooctyl, cyclododecyl, allyl, or benzyl.

3. A process according to claim 1 wherein $R_3$ is n-tetradecyl.

4. A process according to claim 1 wherein $R_3$ is n-decyl.

5. A process according to claim 1 wherein $R_3$ is n-octyl.

6. A process according to claim 1 wherein $R_3$ is cyclopropyl.

7. A process according to claim 1 wherein $R_3$ is cyclohexyl.

8. A process according to claim 1 wherein $R_3$ is cyclooctyl.

9. A process according to claim 1 wherein $R_3$ is cyclododecyl.

10. A process according to claim 1 wherein $R_3$ is allyl.

11. A process according to claim 1 wherein $R_3$ is benzyl.

12. A tobacco product comprising tobacco and from about 0.1 to 500 ppm by weight of at least one N-substituted pyrrole according to claim 1.

13. A tobacco product as defined in claim 12 wherein said pyrrole is N-cyclopropyl pyrrole.

14. A tobacco product as defined in claim 12 wherein said pyrrole is N-cyclooctyl pyrrole.

15. A tobacco product as defined in claim 12 wherein said pyrrole is N-tetradecyl pyrrole.

* * * * *

UNITED STATES PATENT AND TRADEMARK OFFICE
CERTIFICATE OF CORRECTION

PATENT NO. : 3,980,089
DATED : September 14, 1976
INVENTOR(S) : Alan O. Pittet; John V. Pascale; Denis E. Hruza It is certified that error appears in the above-identified patent and that said Letters Patent are hereby corrected as shown below:

Column 6, line 35:  "frutiy" should read --- fruity ---

Column 8, line 33:  "2,5-diemt-" should read --- 2,5-dimet- ---

Column 16, line 28: "(m/c) should read --- (m/e) ---

Signed and Sealed this

Ninth Day of May 1978

[SEAL]

Attest:

RUTH C. MASON
Attesting Officer

LUTRELLE F. PARKER
Acting Commissioner of Patents and Trademarks